United States Patent
Kohnle et al.

(10) Patent No.: US 9,192,954 B2
(45) Date of Patent: Nov. 24, 2015

(54) DISCHARGING APPARATUS FOR MEDIA

(75) Inventors: Joerg Kohnle, Villingen-Schwenningen (DE); Joachim Koerner, Uhldingen-Muehlhofen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 14/234,168

(22) PCT Filed: Jun. 15, 2012

(86) PCT No.: PCT/EP2012/061519
§ 371 (c)(1),
(2), (4) Date: Jan. 22, 2014

(87) PCT Pub. No.: WO2013/013890
PCT Pub. Date: Jan. 31, 2013

(65) Prior Publication Data
US 2014/0144946 A1    May 29, 2014

(30) Foreign Application Priority Data
Jul. 27, 2011 (DE) .......................... 10 2011 079 949

(51) Int. Cl.
*A61M 11/00* (2006.01)
*B05B 11/00* (2006.01)
(Continued)

(52) U.S. Cl.
CPC .......... *B05B 11/3042* (2013.01); *A61M 15/008* (2014.02); *A61M 15/009* (2013.01);
(Continued)

(58) Field of Classification Search
CPC .................................. B67D 7/22; A61M 11/00
USPC .......... 222/36, 38, 182–183; 604/21; 128/203.12, 203.15, 203.23, 200.12, 128/200.23–200.24, 205.23; 377/6, 13, 377/15–16
See application file for complete search history.

(56) References Cited

U.S. PATENT DOCUMENTS 2,239,717 A * 4/1941 Pierce et al. ............ 369/148
5,564,414 A   10/1996 Walker et al.
(Continued)

FOREIGN PATENT DOCUMENTS

CN    1705498 A    12/2005
DE    603 12 026 T2    11/2007
(Continued)

OTHER PUBLICATIONS

Form PCT/ISA/210 International Search Report issued in International Application No. PCT/EP2012/061519 with English translation, date of mailing Oct. 2, 2012 (6 pages).
(Continued)

*Primary Examiner* — Paul R Durand
*Assistant Examiner* — Andrew P Bainbridge
(74) *Attorney, Agent, or Firm* — Flynn, Thiel, Boutell & Tanis, P.C.

(57) ABSTRACT

A discharging apparatus having two housing portions displaceable in relation to one another, a discharging opening for discharging a medium, and a reservoir for storing the medium. A manual displacement movement of the housing portions causes medium to be delivered from the reservoir to the discharging opening. The discharging apparatus has an electric load, an electromagnetic generator by which the mechanical energy introduced upon actuation is converted into electrical energy for supplying the electric load, and the electromagnetic generator has a magnet and a conductor connected to the electric load.

A spring energy store with a stressing member movable in relation to the second housing portion, and a spring acting between the second housing portion and the stressing member are provided.

12 Claims, 5 Drawing Sheets

(51) Int. Cl.
*A61M 15/00* (2006.01)
*B05B 12/00* (2006.01)
*H02K 7/18* (2006.01)

(52) U.S. Cl.
CPC ............ *B05B11/308* (2013.01); *B05B 12/004* (2013.01); *H02K 7/1853* (2013.01); *A61M 2205/825* (2013.01); *B05B 11/0037* (2013.01)

(56) References Cited

U.S. PATENT DOCUMENTS

| | | | | |
|---|---|---|---|---|
| 5,755,218 | A * | 5/1998 | Johansson et al. | 128/200.14 |
| 5,809,997 | A * | 9/1998 | Wolf | 128/200.23 |
| 6,029,659 | A * | 2/2000 | O'Connor | 128/203.12 |
| 8,240,301 | B2 * | 8/2012 | Spaargaren et al. | 128/200.23 |
| 8,267,086 | B2 | 9/2012 | Bruna | |
| 8,739,790 | B2 * | 6/2014 | Bruna | 128/205.23 |
| 2005/0284471 | A1 | 12/2005 | Bruna | |
| 2006/0011651 | A1 * | 1/2006 | Bruna | 222/36 |
| 2007/0017506 | A1 * | 1/2007 | Bell et al. | 128/200.23 |
| 2007/0135756 | A1 * | 6/2007 | Kohlbrenner et al. | 604/21 |
| 2008/0185395 | A1 * | 8/2008 | Sahud | 222/36 |
| 2009/0151721 | A1 * | 6/2009 | Spaargaren et al. | 128/203.12 |
| 2009/0200983 | A1 * | 8/2009 | Dyer et al. | 320/107 |

FOREIGN PATENT DOCUMENTS

| | | |
|---|---|---|
| EP | 1 559 083 B1 | 8/2005 |
| WO | WO 03/020349 A2 | 3/2003 |
| WO | WO 2007/137991 A1 | 12/2007 |

OTHER PUBLICATIONS

First Office Action of Chinese Patent Office issued in Application No. 201280037385.8 with English translation dated May 28, 2015 (9 pages).

* cited by examiner

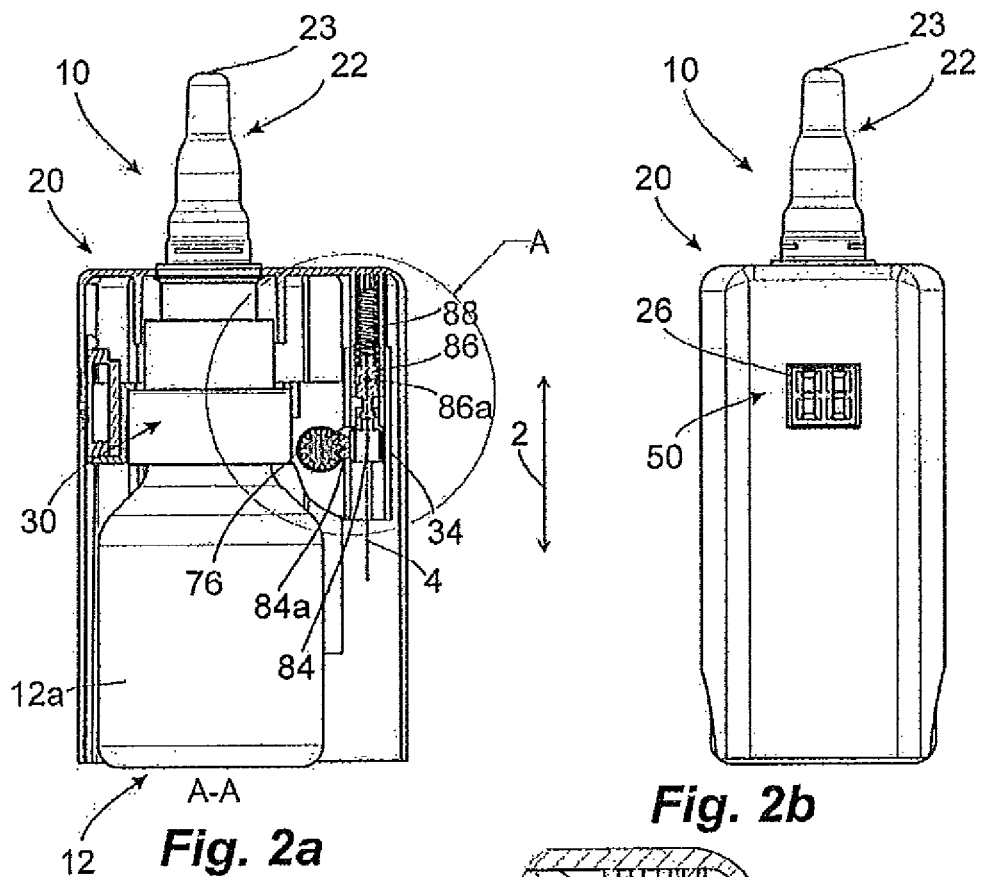
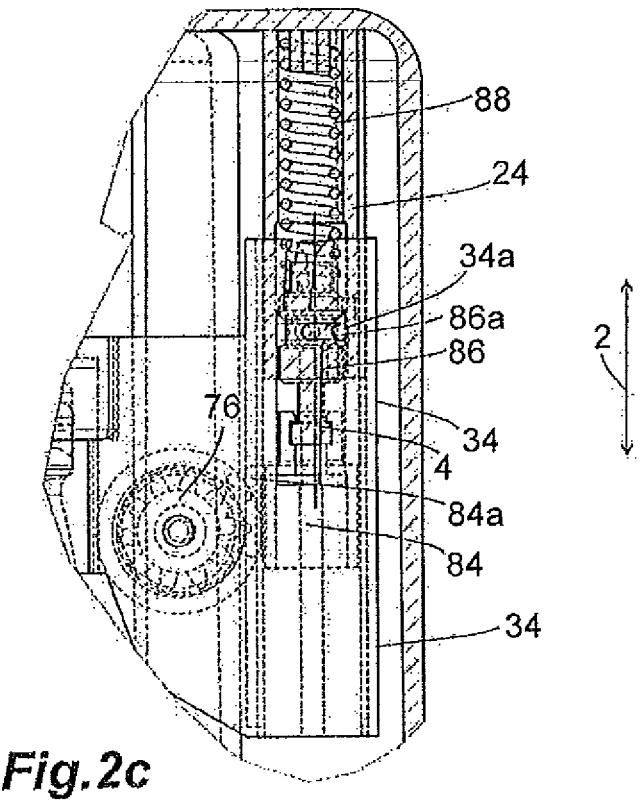
Fig. 2a
Fig. 2b
Fig. 2c

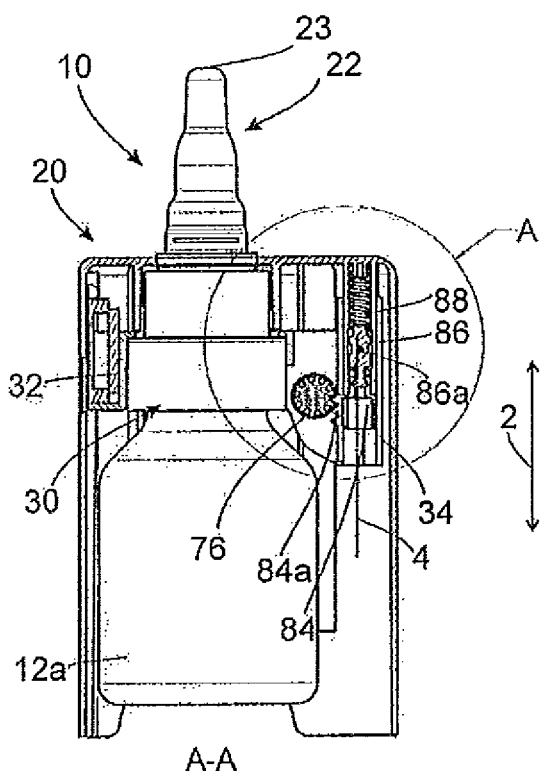
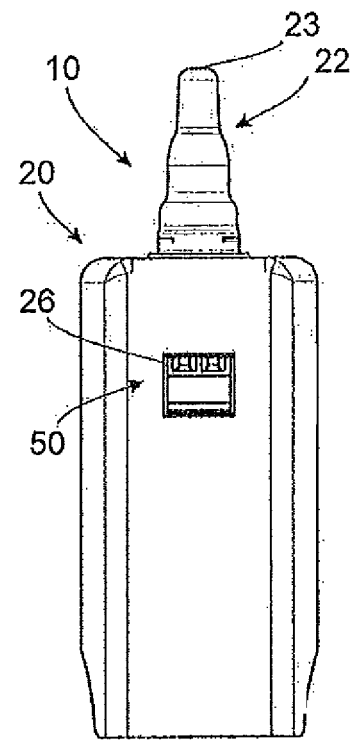
Fig. 4a    Fig. 4b
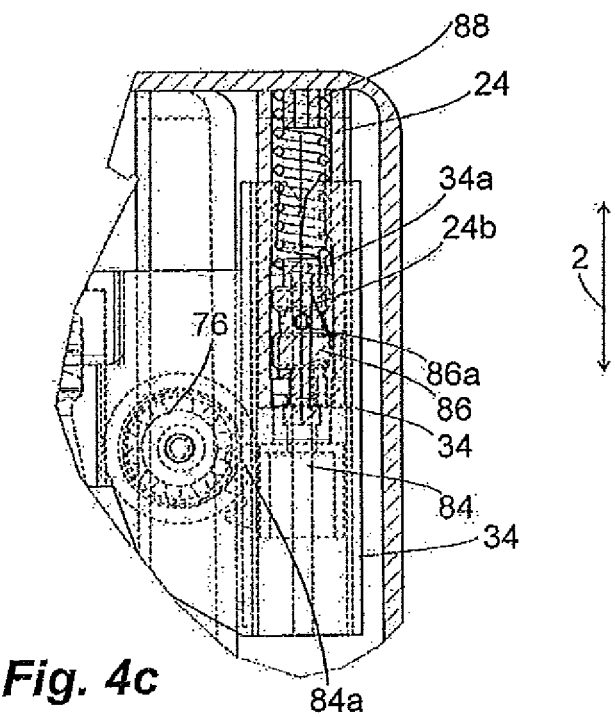
Fig. 4c

DISCHARGING APPARATUS FOR MEDIA

APPLICATION AREA AND PRIOR ART

The invention relates to a discharging apparatus for liquid, pasty or pulverulent media, having a housing with a first housing portion and a second housing portion, which are displaceable in relation to one another for actuating purposes, having a discharging opening for discharging the medium, and having a reservoir for storing a medium prior to being discharged. It is provided here, in the case of a discharging apparatus of the type in question, that a manual displacement movement of the housing portions in relation to one another can cause medium to be delivered from the reservoir to the discharging opening. It is also provided that the discharging apparatus has an electric load and an electromagnetic generator, by means of which some of the mechanical energy introduced upon actuation is converted into electrical energy for supplying the electric load. Such an electromagnetic generator here, in the manner of a dynamo, has a component which comprises a magnet and a second component which comprises a conductor, in particular in the form a coil, connected to the electric load, wherein one of the components is provided at a fixed location in relation to one of the housing portions and one of the components is provided such that it can be moved in relation to the fixed-location component, and therefore a relative movement of the components allows current to be generated.

Discharging apparatuses of the type in question can be used for discharging various media, the discharging apparatus preferably being one which is filled with a pharmaceutical medium and provided for discharging said medium. Such discharging apparatuses of the type in question are usually used by the patient or the user himself. They are portable units which can readily be taken anywhere.

The discharging operation, in the case of discharging apparatuses of the type in question, is made possible by the displaceability of two housing portions. This displacement movement of the housing portions causes discharging to take place, and this can be realized, for example, by a pump, in particular, for example, a piston pump, being actuated by the displacement movement. Alternative configurations, however, may also provide for the displacement movement to open just a discharging valve, through which medium which is already stored under pressure in the discharging apparatus can flow to the discharging opening and pass into the surrounding atmosphere.

Provision is made for discharging apparatuses of the type in question to have an electric load. Such discharging apparatuses with an electric load are becoming increasingly common. The electric loads may comprise, for example, an electronic counter and indicators such as a liquid-crystal display, LEDs or the like. Also a blocking mechanism, which, following a discharging operation, prevents any further discharging operation for a certain period of time, usually comprises at least one electric load. Radio transmitters and sensor devices are also possible electric loads, in order to monitor the correct use of the dispenser.

Provision is made for dispensers of the type in question which have such an electric load to have, for the purpose of supplying power to the electric load, a converter, by means of which the mechanical energy introduced manually by the displacement movement is converted into electrical energy. There are various proposals in the prior art relating to such converters. For example, DE 60312026 T2 already proposes to make use, in a manner similar to a conventional lighter, of a piezoelectric converter. As an alternative to this, WO 2007/137991 A1 discloses using an electromagnetic generator, in a manner corresponding to the configuration of the type in question. An electromagnetic generator in this context is understood to mean a sub-component which induces a voltage in a current-channeling conductor or a coil by the movement of a permanent magnet relative to said conductor or coil.

WO 2007/137991 A1 proposes a rotary-operation generator, wherein the coupling of said generator to the relative movement of the actuating handle provided there takes place by way of a rack, which is fitted at a fixed location on the actuating handle and meshes with a gearwheel of the generator. The problem with this known configuration is that, in the case of particularly small generators which can be used for discharging apparatuses of the generic type, a comparatively high efficiency can be achieved only when said generators are operated at high speeds. The solution known from WO 2007/137991 A1 cannot systematically ensure these high speeds since the situation where a user pushes the actuating handle downward very slowly cannot be ruled out. Although, even in this case, the two components of the generator would be moved in relation to one another, only a small amount of electrical energy would be generated on account of the low speed.

OBJECT AND SOLUTION

It is an object of the invention to develop a discharging apparatus of the type in question to the extent that it supplies a greater quantity of electrical energy per actuation and supplies this quantity of energy, in particular, in a reproducible manner.

For this purpose, the invention provides for a discharging apparatus according to the invention to have a spring energy store with a stressing member, which can be moved in relation to a second housing portion, and a spring, which acts between the second housing portion and the stressing member. The stressing member here is designed to be coupled to the first housing portion during a displacement movement, and therefore the spring is subjected to stressing during the displacement movement. It is also provided that, in the at least partially stressed state of the spring, the stressing member can be uncoupled from the first housing portion, and this therefore allows the spring to be relieved of stressing. As the spring is being relieved of stressing in this way, according to the invention, the stressing member is operatively coupled to the movable component of the generator at least in certain phases, and therefore the movement of the stressing member causes the movable component of the generator to move in relation to the fixed-location component of the generator.

The invention thus provides for the first housing portion, the second housing portion and the stressing member of the spring energy store to provide a total of three sub-devices which are moved in relation to one another in each case, at least in certain phases, for the purpose of driving the movable component of the generator. During the movement of the housing portions relative to one another, this also causing the discharging operation of the medium, the stressing member is coupled to the first housing portion, and therefore the stressing member is moved, together with said first housing portion, in relation to the second housing portion. The spring-energy-store spring, which is preferably designed as a compression spring, is subjected to stressing in the process, since it is connected not just to the stressing member, but also to the second housing portion, or is supported thereon. In the at least partially stressed state of the spring, and preferably in a defined position of the two housing portions relative to one another, the stressing member is uncoupled from the first housing portion, preferably in an automatically distance-controlled, force-controlled or energy-controlled manner, and therefore the stressing member resumes its starting position, or is shifted at least in the corresponding direction, relative to the second housing portion under the action of the stored spring energy. Operative coupling to the movable component of the generator is provided at least during a sub-phase of this movement, and therefore said movable component is moved in relation to the component which is preferably of a fixed location in relation to the second housing portion, said second component generating current as a result.

Since the relative movement of the stressing member following uncoupling from the first housing portion, and relative to the second housing portion, takes place at least largely irrespective of whether the movement of the housing portions in relation to one another has previously taken place quickly or slowly, a largely reproducible movement of the components of the generator relative to one another is achieved. Furthermore, an appropriate selection of the spring characteristics can cause the stressing member to move quickly relative to the second housing portion following uncoupling from the first housing portion. The high speed and the high reproducibility make it possible to achieve a high efficiency, and therefore a comparatively large amount of energy is available for supplying the electric load.

This energy need not be fed directly to the electric loads. Use may be made of voltage-adaptation components, for example a rectifier, a voltage transformer, or also interim stores, such as a buffer capacitor or a buffer battery.

The stressing member, in the case of one configuration according to the invention, can be moved in a same movement direction in relation to the housing portions as the latter can be moved in relation to one another. The most straightforward configuration of the operative coupling between the stressing member and the movable component of the generator thus provides that said movable component is provided directly on the stressing member and can thus also be moved linearly in relation to the first housing portion. In such a case, the generator would have to be designed as a linear generator. It would thus be possible in particular for the permanent magnet to be fixedly connected to the stressing member and thus, during the movement of the stressing member in relation to the first housing portion, likewise to be moved in relation to a coil provided on the first housing portion. An advantageous configuration, however, is one in which the movable component of the electromagnetic generator is mounted such that it can be rotated in relation to the fixed-location component. In this case, however, it is necessary to have a transmission unit, which converts the linear movement of the stressing member into a rotary movement of the movable component of the generator. Said transmission unit preferably comprises a linearly extending toothing formation on the stressing member and a gearwheel, which is connected in particular coaxially, and preferably in a fixed manner, to the movable component of the generator.

It is also possible, in principle, for the operation of uncoupling the first housing portion from the stressing member, once the spring has been subjected to stressing, to take place manually. In the case of such a configuration, the spring would be subjected to stressing during the displacement movement of the housing portions and then would be relieved of stressing only when this is brought about by the user manually actuating a, for example, separate handle. A preferred configuration, however, is one in which the stressing member is uncoupled automatically from the first housing portion, wherein preferably the stressing member and the first housing portion are co-ordinated with one another such that, in a defined uncoupling position of the displacement movement, the stressing member is uncoupled automatically. Electrical energy is thus always generated directly during the course of the actuation of the discharging apparatus and in reaction to the user-induced actuating movement. This is expedient since it is thus possible, for example immediately following a discharging operation, for a counting register to be updated and the content thereof to be output on a liquid-crystal display.

As already mentioned, it is mostly advantageous to have relatively high rotational or linear speeds for generators of very small construction. The uncoupling position and the spring of a discharging apparatus according to the invention are therefore co-ordinated with one another preferably such that, as the spring is being relieved of stressing, the moving component of the generator, in the case of a linear generator, reaches at least a speed of 800 mm/s, preferably of 1000 mm/s, in particular preferably of at least 1200 mm/s. In the case of a rotary generator, it is advantageous if a rotational speed of at least 30 revs/sec is reached. Also advantageous, in contrast, are speeds of revolution of at least 50 revs/sec, in particular preferably of at least 80 revs/sec. The speed is influenced, on the one hand, by the transmission unit, which is located upstream of the generator, and on the other hand by the configuration of the spring and that position of the housing portions relative to one another in which uncoupling takes place.

The operative coupling, which takes place, according to the invention, at least in certain phases between the movement of the stressing member and the movement of the movable component of the generator, may also be provided in the form of permanent operative coupling, in which case the stressing member and the movable component of the generator are always moving at the same time. In contrast, however, an advantageous configuration may be one in which the operative coupling is such that it terminates, following uncoupling, even prior to the stressing member reaching a standstill. It is thus the case with such a configuration that, as the spring is being relieved of stressing, the stressing member comes out of engagement with the movable component of the generator. This allows the movable component of the generator to continue running. The standstill state of the stressing member, which occurs in the end position, does not bring about an immediate standstill of the movable component of the generator. It is therefore the case that a relatively small amount of the mechanically introduced energy is converted into heat energy and a higher fraction is available for generating electrical energy. In particular, a toothing formation can be used to provide such operative coupling, achieved only in certain phases, between the stressing member and the movable component of the generator, wherein the two parts which carry the toothing formations are disengaged from one another prior to the stressing member coming to a standstill.

In the case of a particularly preferred configuration, the two housing portions can be moved in relation to one another in an actuating direction which encloses an angle between 70° and 110° with a main direction of extent of the discharging apparatus, this latter direction being defined by a discharging direction of the medium. The apparatus is thus designed in the form of a so-called side-actuation apparatus. This has been found to be advantageous in respect of the amount of installation space available and the utilization thereof. It is also the case that such discharging apparatuses can be handled more ergonomically.

As already outlined, a discharging apparatus according to the invention preferably has a delivery pump for delivering the medium to the discharging opening or else has an outlet valve for letting the medium out of the discharging apparatus.

This delivery pump, or this discharging valve, is preferably designed such that, during the course of a displacement movement, the medium is only discharged for the first time beyond the uncoupling position.

Upon actuation, it is therefore the case that medium is discharged only when energy has already been generated. This is advantageous, in particular, in conjunction with electronic counting of the discharging operations, since it ensures that the energy necessary for counting purposes is available. Discharging medium upstream of the uncoupling position involves the risk that, although incomplete actuation does indeed cause the medium to be discharged, it is not possible for any counting to be provided for the same.

In other configurations, in particular in configurations in which the generation of energy does not serve the primary purpose of counting, it may be advantageous to provide the uncoupling position within the final 10% of the displacement path, in order thus for the greatest possible quantity of mechanical energy to be stored in the spring before the generation of energy begins.

BRIEF DESCRIPTION OF THE DRAWINGS

Further aspects and advantages of the invention can be gathered not just from the claims, but also from the following description of a preferred exemplary embodiment of the invention, this exemplary embodiment being explained with reference to the figures, in which:

FIGS. 2a to 2c show the discharging apparatus from FIG. 1 prior to a discharging actuation beginning, FIGS. 4a to 4c show the discharging apparatus during a main phase of the generation of electrical energy.

DETAILED DESCRIPTION OF THE EXEMPLARY EMBODIMENT

Figure 1:
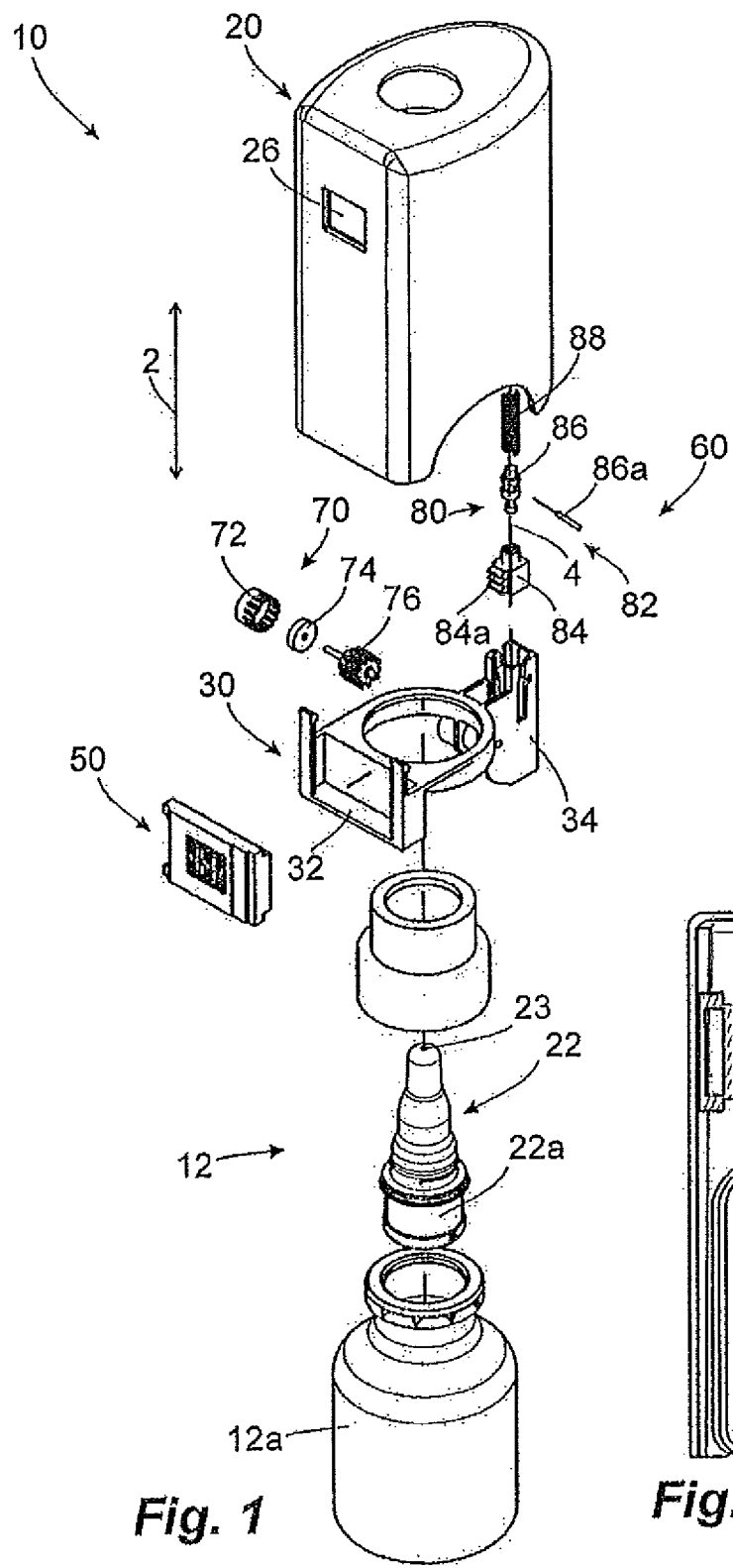
FIG. 1 shows an exploded illustration of a discharging apparatus according to the invention.

FIG. 1 shows an exploded illustration of one embodiment of a discharging apparatus according to the invention. This FIG. 1, FIG. 1a and FIG. 2a will be used to highlight, in the first instance, the essential components of this discharging apparatus 10.

The discharging apparatus 10 has a two-part housing with an inner, first housing portion 30 and an outer, second housing portion 20. The outer housing portion 20 forms the predominant part of the externally visible surfaces of the discharging apparatus and has a discharging extension 22, at the distal end of which a discharging opening 23 is provided. The inner housing portion 30 can be moved relative to said outer housing portion 20 in the direction symbolized by the arrow 2. The inner housing portion 30 is formed essentially by a carrier 32 and the liquid store 12a of a pumping dispenser 12, to which the discharging extension 22 of the outer housing portion 20 also belongs. The pumping dispenser 12 is designed to bring about a discharging operation through the discharging opening 23 when the discharging extension 22 is shifted in direction 2 in relation to the liquid store 12a. For this purpose, the pumping dispenser has a pump 22a.

The discharging apparatus also has an electronic counter module 50, which is provided on the inner housing portion 30, wherein the outer housing portion 20 contains a viewing window 26, through which it is possible to read off a liquid-crystal display or a bistable display of the counter module 50.

In order to supply power to the counter module and the electronic components thereof, the discharging apparatus has a current-generating unit 60. Said current-generating unit 60 comprises, as its main component, an electromagnetic generator 70 and also a drive device 80 for the generator 70. The generator 70 has a stator 72 with coil windings (not illustrated), wherein said stator 72 is fitted at a fixed location in relation to the housing portion 30. It also has a rotor 74 with a permanent magnet rotating within the windings of the stator 72. Rotation of the rotor 74 in relation to the stator 72 can generate electrical energy, which is routed to the counter module 50 via lines (not illustrated).

The rotor 74 can be made to rotate in relation to the stator 72 by means of a gearwheel 76, which is rotationally fixed in relation to the rotor, in order thus to generate the electrical energy for supplying the counter module 50. The drive device 80 provided for this purpose comprises three sub-devices, which can be moved relative to one another in relation to the direction 2. The first of these three sub-devices is an accommodating shaft 34, which extends in direction 2, is open to the side of the generator 70 and is part of the inner housing portion 30. The second sub-device is a hollow extension 24, which is pushed into said shaft 34, and can be moved within the shaft 34, and is provided at a fixed location on the outer housing portion 20. The third sub-device is a stressing member 82, which is likewise accommodated, at least predominantly, within the shaft 34 and can be moved relative to the extension 24 to a limited extent in respect of the direction 2. The stressing member 82 here comprises a drive portion 84, which is adapted to the shaft 34 such that it cannot be rotated in relation to the same. The stressing member 82 also comprises a triggering portion 86 with a radially outwardly oriented triggering pin 86a. The triggering portion 86 can be moved, together with the drive portion 84, in the direction 2. In addition, it can be rotated about the vertical axis 4 in relation to the drive portion 84. A compression spring 88 is provided within the extension 24, between the stressing member 82 and the base on the upper side of the extension 24. The drive portion 84 of the stressing member has a short rack 84a which in the starting position, which is illustrated in FIG. 2a, is already in engagement with the gearwheel 76.

Figure 1A:
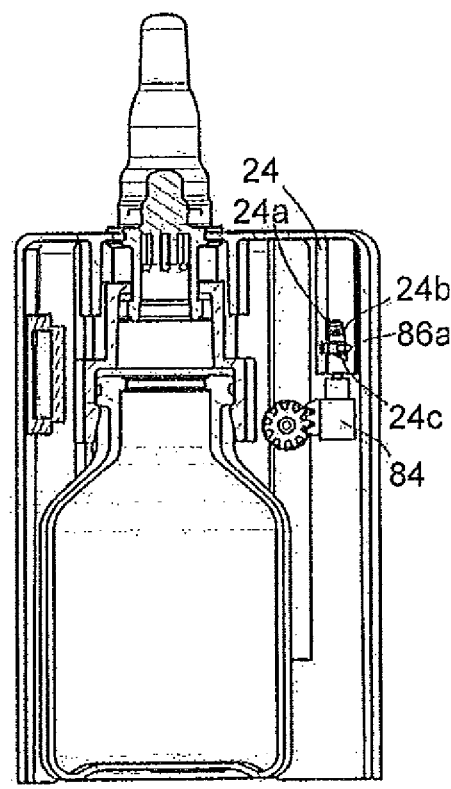
FIG. 1a shows the discharging apparatus from FIG. 1 in a sectional illustration with the inner housing portion partially blanked out.

FIG. 1a highlights the limited movement capability of the stressing member 82 relative to the extension 24. The extension 24 has an aperture 24a, through which the triggering pin 86a projects. Said aperture 24a has two slopes 24b, 24c. The upper slope 24b is suitable for rotating the triggering pin 86a, together with the triggering portion 86, to the left, as seen in relation to the illustration, when the extension 24 is shifted downward in relation to the triggering portion 86. This will be explained in more detail. The lower slope 24c is suitable for rotating the triggering pin 86a, together with the triggering portion 86, back to the right when the triggering portion is pushed against said lower slope 24c by means of the spring 88.

The drive device 80 is provided so that, during the course of a manual actuation of the discharging apparatus 10, in the first instance at least some of the mechanical energy introduced into the system here is stored in the spring 88. Some of this stored energy is then converted into electrical energy for the counter module 50.

Specifically, this takes place as follows:

Starting from the state of FIGS. 2a to c, the housing portions 20, 30 are moved relative to one another in the direction of the arrow 2, wherein, as seen in relation to the perspective of FIG. 2a, the outer housing portion 20 is pushed downward and/or the inner housing portion 30 is pushed upward. This takes place preferably in that the user places at least one finger on the upper side of the outer housing portion 20, alongside the discharging extension 22, and a second finger, or the thumb, on the underside of the liquid store 12a, and then forces the two parts of the housing toward one another, which results in movement of these two parts relative to one another.

FIGS. 3a-5c show different stages of this actuating movement, wherein this actuating movement, in the customary manner known from the prior art, causes medium to be discharged out of the medium store 12a, through the discharging opening 23, into the surroundings.

Starting from FIG. 2a, the aforementioned relative movement of the housing portions 20, 30 inevitably results in the extension 24 being shifted in relation to the shaft 34, since the shaft 34 and the extension 24 are each provided at a fixed location on a respective housing portion 20, 30. The stressing member 82 remains, in the first instance, in that position relative to the inner housing portion 30 which is illustrated in FIG. 2a, since the triggering pin 86a is arranged within a horizontal recess 34a of the wall of the shaft 34 and the stressing member 82 is thus secured on the inner housing portion 30, as seen in relation to the direction 2. During this first phase, there is no electrical energy generated, since it is also the case that the toothing formation 84a does not move with the stressing member 82 in relation to the generator 70.

Figure 3A:
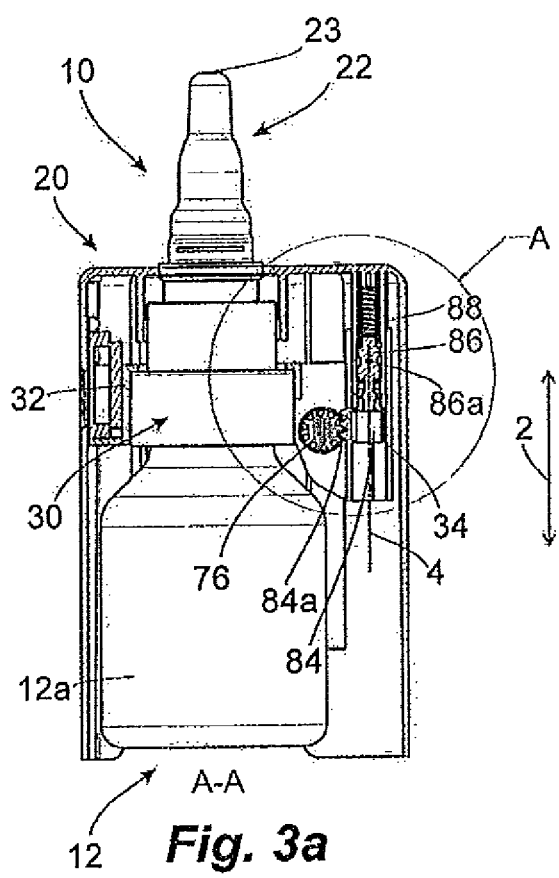
FIGS. 3a to 3c show the discharging apparatus just prior to an internal stressing member being triggered for generating electrical energy.
Figure 3B:
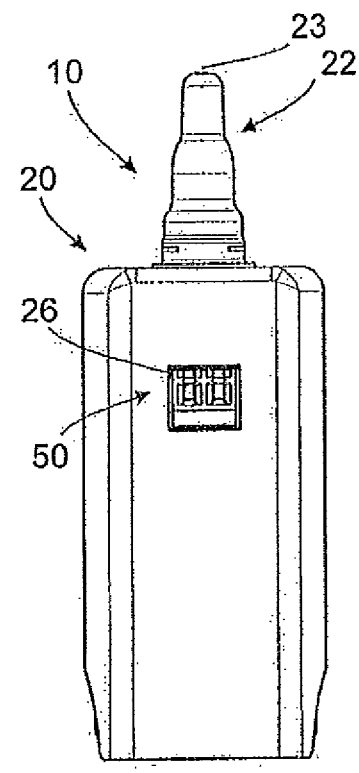
Figure 3C:
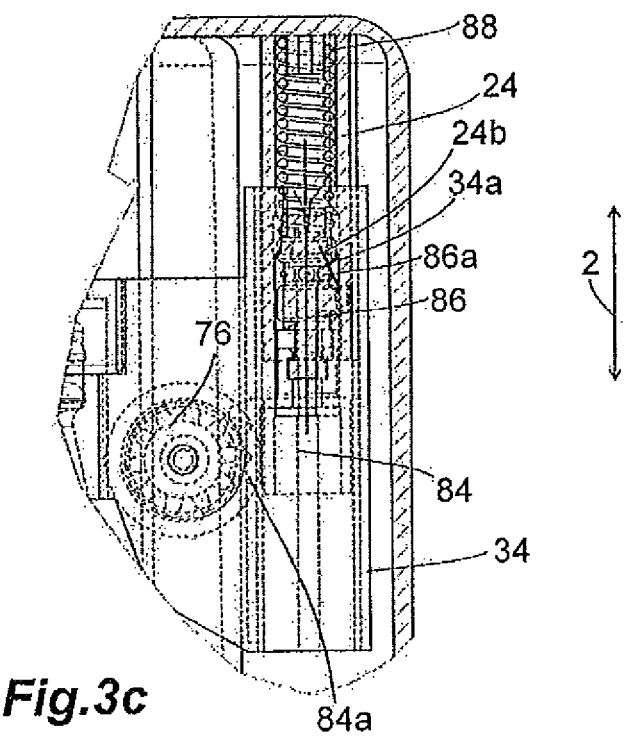

The continued movement of the housing portions 20, 30 in relation to one another causes the triggering pin 86a to be pushed downward to an increasing extent to the left, out of the recess 34a, wherein this takes place by means of the slope 24b on the extension 24, said slope being depicted in FIG. 3c and being shifted together with the outer housing portion 20 as a result of the relative movement of the housing portions 20, 30. This movement of the triggering pin 86a is made possible by the ability of the triggering portion 86 to rotate in relation to the drive portion 84 of the stressing member 82.

FIGS. 3a and 3c, in particular FIG. 3c, show the changed position of the triggering pin 86a in relation to the recess 34a as the actuating movement continues.

In this first phase of the actuation, as the triggering pin 86a is located in the recess 34a, the inner housing portion 30 and the stressing member 82 inevitably move together, and this results in the spring 88 being subjected to stressing, said spring being compressed as the relative movement of the housing portions 20, 30 continues.

As soon as the housing portions 20, 30 have been shifted to the extent where the triggering pin 86a has been pushed downward all the way to the left, out of the recess 34a, by means of the slope 24b, a second phase of the actuation follows, this being illustrated in FIGS. 4a-4c and forming the main current-generating phase. In this main current-generating phase, the spring 88, which is subjected to stressing, releases the spring energy stored in it and thus pushes the stressing member 82 downward in relation to the outer housing portion 20 and in particular also in relation to the inner housing portion 30. As a result of the movement of the stressing member 82 relative to the inner housing portion 30, in this phase, the rack 84a also moves in relation to the generator 70 and thus drives the gearwheel 76. Since this is brought about predominantly by the prestressed spring 88, a very high speed is reached here. The gearwheel and thus the rotor of the generator 70 are accelerated to approximately 5000 rpm. This speed is very well suited for generating electrical energy.

Figure 5A:
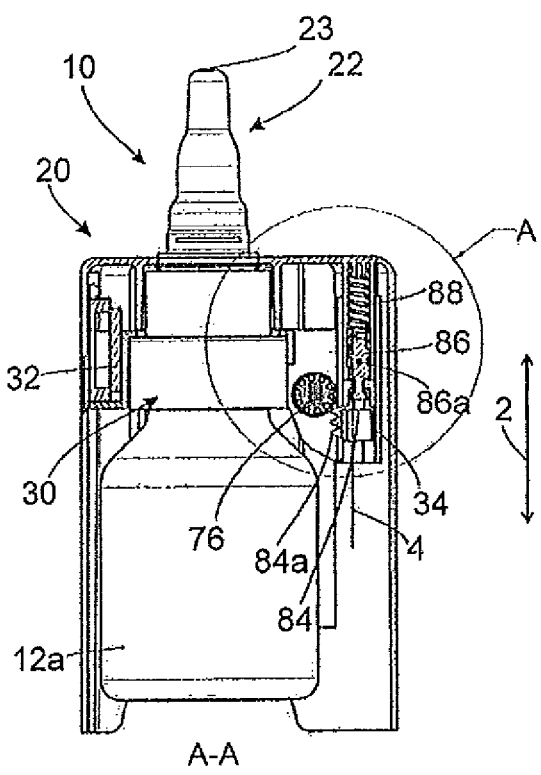
FIGS. 5a to 5c show the discharging apparatus during a continued-running phase for generating electrical energy.
Figure 5B:
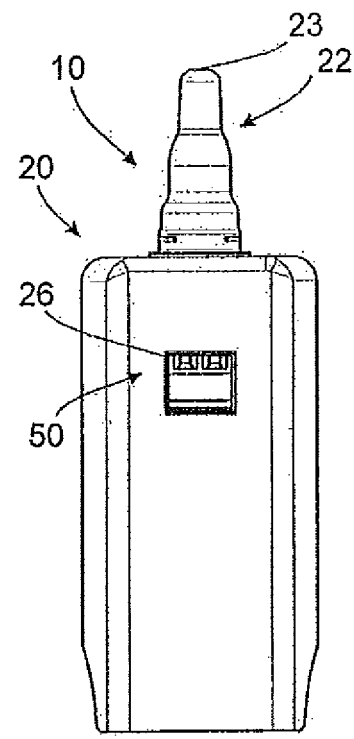
Figure 5C:
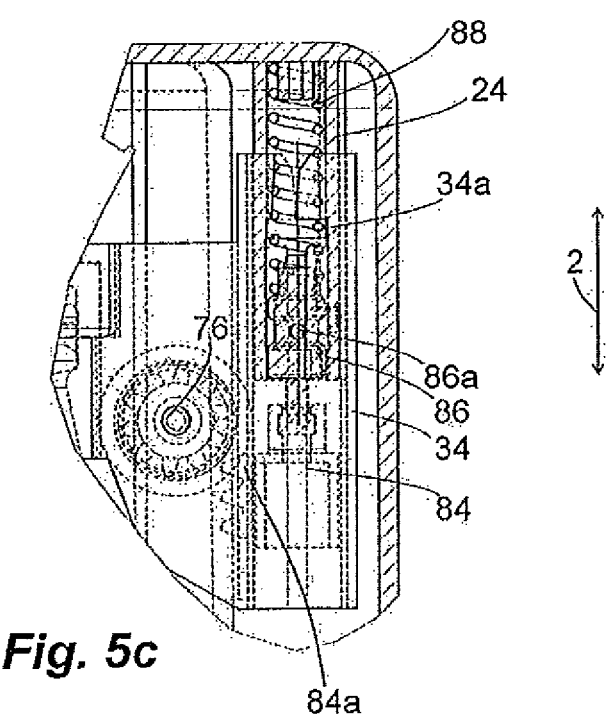

As a result of the continued actuating movement of the housing portions 20, 30 in relation to one another and of the movement of the stressing member 82 relative to the housing portions 20, 30, the rack 84a is disengaged from the gearwheel 76, in a manner illustrated in FIGS. 5a-5c, toward the end of its movement phase. This means that the gearwheel 76, at the point in time at which the stressing member 82 reaches its end position of FIG. 5a-5c, does not abruptly stop its rotary movement, and thus the rotor continues to undergo rotary movement. It is therefore the case that, even once the stressing member 82 has come to a standstill relative to the inner housing portion 30, electrical energy continues to be generated in a continued-running phase. This makes it possible to generate approximately 10% to 25% more electrical energy than when the rack does not disengage from the gearwheel and thus, when the end position of the stressing member 82 in relation to the inner housing portion 30 has been reached, brakes the gearwheel, and thus the rotor, abruptly.

The energy generated is used to increase an electronic counting register in a counter module 50 by one and to indicate the value, at least briefly, on the liquid-crystal display of the counter module 50. If use is made of a bistable display, this value is indicated until the next change is made.

Once the external application of force has been done away with, the housing portions 20, 30 are pushed back again, under the action of an internal restoring spring (not illustrated) within the pumping dispenser 12, into their starting position of FIG. 2. On account of the force of the spring 88, and on account of the slope 24c, the triggering pin 86a is moved back into the recess 34a of the wall of the shaft 34.

In the case of the embodiment illustrated, the stressing member 82 is triggered, and thus the operation of generating electrical energy is begun, even before the housing portions 20, 30 have reached their relative end position. In the case of alternative configurations, however, provision may be made for the triggering to take place only toward the end, that is to say in the region of the final 10% of the displacement path of the housing portions 20, 30 in relation to one another.

The invention claimed is:

1. A discharging apparatus for liquid, pasty or pulverulent media, having
   a housing with a first housing portion and a second housing portion, the first and second housing portions being displaceable in relation to one another;
   a discharging opening for discharging the medium; and
   a reservoir for storing the medium prior to being discharged, wherein a manual displacement movement of the first and second housing portions in relation to one another causes medium to be delivered from the reservoir to the discharging opening;
   an electric load;
   an electromagnetic generator which converts mechanical energy introduced, upon the manual displacement movement of the first and second housing portions in relation to one another, into electrical energy for supplying the electric load, the electromagnetic generator having a component which comprises a magnet and a component which comprises a conductor connected to the electric load, wherein one of the components is a fixed location component provided at a fixed location in relation to one of the first and second housing portions and the other of the components is a movable component movable in relation to the fixed-location component;
   a spring energy store with a stressing member, movable in relation to the second housing portion, and a spring acting between the second housing portion and the stressing member, the stressing member having a coupling position in which the stressing member is coupled to the first housing portion during the manual displacement movement to subject the spring to stressing, the stressing member having an uncoupled position in the stressed state of the spring in which the stressing member is uncoupled from the first housing portion to relieve the spring of stressing, and while the spring is being relieved of stressing, the stressing member is operatively coupled to the movable component of the electromagnetic generator at least in certain phases, the movement of the stressing member causing the movable component to move.

2. The discharging apparatus as claimed in claim 1, wherein the movable component of the electromagnetic generator is mounted for rotation in relation to the fixed-location component.

3. The discharging apparatus as claimed in claim 1, wherein the stressing member and the first and second housing portions are designed, and co-ordinated with one another, such that, when a defined position of the manual displacement movement is reached, the stressing member is uncoupled automatically from the first housing portion.

4. The discharging apparatus as claimed in claim 3, wherein the defined position and the spring are co-ordinated with one another such that, as the spring is being relieved of stressing, the moving component of the electromagnetic generator reaches at least a maximum speed of 800 mm/sec or at least a maximum rotational speed of 30 revolutions/sec.

5. The discharging apparatus as claimed in claim 1, wherein, as the spring is being relieved of stressing, the stressing member is operatively coupled to the movable component of the electromagnetic generator, wherein said operative coupling terminates prior to the stressing member reaching a standstill.

6. The discharging apparatus as claimed in claim 1, wherein the operative coupling between the stressing member and the movable component takes place via toothing formations provided on the movable component and on the stressing member.

7. The discharging apparatus as claimed in claim 1, wherein the first and second housing portions are movable in relation to one another in an actuating direction which encloses an angle between 70° and 110° with a main direction of extent of the discharging apparatus, the main direction of extent being defined by a discharging direction of the medium.

8. The discharging apparatus as claimed in claim 1, wherein a delivery pump is provided for delivering the medium to the discharging opening or an outlet valve is provided for letting the medium out of the discharging apparatus.

9. The discharging apparatus as claimed in claim 8, wherein the delivery pump or the outlet valve is designed such that the medium discharges, during the course of the manual displacement movement, beyond the uncoupled position.

10. The discharging apparatus as claimed in claim 1, wherein the manual displacement movement of the first and second housing portions relative to one another has a first phase in which the stressing member and the first housing portion are in the coupling position and move together to cause the spring to store energy, and a second phase in which the stressing member and the first housing portion are in the uncoupled position in which the stressing member moves relative to the first and second housing portions to release energy stored in the spring.

11. The discharging apparatus as claimed in claim 10, wherein in the second phase of the manual displacement movement the stressing member operatively couples with the movable component of the electromagnetic generator and moves the movable component, the electromagnetic generator converting mechanical energy introduced by movement of the stressing member in the second phase of the manual displacement movement into electrical energy to supply the electric load.

12. The discharging apparatus as claimed in claim 11, wherein at a defined position of the manual displacement movement in the second phase thereof, the stressing member automatically uncouples from the first housing portion and moves relative to both the first and second housing portions to release energy stored in the spring.

* * * * *